United States Patent [19]

Seidman et al.

[11] Patent Number: 5,589,369
[45] Date of Patent: Dec. 31, 1996

[54] CELLS HOMOZYGOUS FOR DISRUPTED TARGET LOCI

[75] Inventors: Jonathan G. Seidman, Milton, Mass.; Aya Jakobovits, Menlo Park, Calif.

[73] Assignees: Cell Genesys Inc., Foster City, Calif.; The President and Fellows of Harvard College, Cambridge, Mass.

[21] Appl. No.: 252,048

[22] Filed: May 31, 1994

Related U.S. Application Data

[63] Continuation of Ser. No. 833,992, Feb. 11, 1992, abandoned.

[51] Int. Cl.⁶ .............................. C12N 15/00; C12N 5/00
[52] U.S. Cl. .................................... 435/172.3; 435/240.1; 435/172.1
[58] Field of Search ............................... 435/172.3; 800/2

[56] References Cited

PUBLICATIONS

Zijlstra et al (1989) Nature 342, 435–438.
Blomberg et al (1982) Proced. Natl. Acad. Sci. 79, 530–533.
Paluean et al (1989) Gene 85, 421–426.
Campbell and Worton (1981) Mo. Cell. Bio. 1:336–346. Segregation of recessive phenotypes on somatic cell hybrids: Role of mitoic recombination, gene inactivation and chromosomal non–disjunction.
T. Rajan, et al. (1990) J. Imm. 145:1598–1602. Rate and mechanism of generation of β2–microglobulin mutants from a heterozygous murine cell line.
T. Potter, et al. (1987) P.N.A.S. 84:1634–1637. Mitotic recombination between homologous chromosomes generates H–2 somatic cell variants in vitro.
F. Nelson, et al. (1989) M. C. Bio. 9:1284–1288. Mitotic recombination is responsible for the loss of heterozygosity in cultured murine cell lines.
K. Paludin, et al. (1989) Gene 85:421–426. Gradauted resistance to G418 leads to differential selection of culture mammalian cells expressing the neo gene.
R. Mortenson, et al. (1991) P.N.A.S. 88:7036–7040. Embryonic stem cells lacking a functional inhibitory G–protein subunit produced by gene targeting of both alleles.

Primary Examiner—Jacqueline M. Stone
Assistant Examiner—Deborah Crouch
Attorney, Agent, or Firm—Karen I. Krupen

[57] ABSTRACT

Homozygotic cells are obtained by employing homologous recombination with a construct comprising a marker gene. The marker gene allows for selection without amplification and by employing elevated levels of the antibiotic to which the marker gene imparts resistance, gene conversion can occur, where in a diploid host, both copies of the target locus will be the same. In this manner, knock-outs of genes can be readily achieved without requiring two steps of homologous recombination.

11 Claims, No Drawings

CELLS HOMOZYGOUS FOR DISRUPTED TARGET LOCI

This is a continuation of application Ser. No. 07/833,992 filed Feb. 11, 1992, now abandoned.

TECHNICAL FIELD

The field of this invention is directed targeting of genes in viable cells.

BACKGROUND

There are continuing advances in the ability to modify cells. One of the most exciting areas for the treatment of genetic diseases is gene therapy. In those situations where cells can be isolated, which are relatively long-lived and can be grown in culture and expanded, one has the opportunity to isolate such cells from a host, either the diseased host or an allogeneic host. The cells may then be grown in culture, expanded, and modified by homologous recombination, and the modified cells restored to the host.

In other situations, one wishes to produce products which are exogenous to the host. In this situation, one may modify embryonic stem cells, add them to a blastocyst, and then produce a chimeric host. This chimeric host may then be mated and the progeny either used as heterozygous mutants or further mated to produce homozygous mutants. By providing for appropriate changes in the embryonic cells, one can produce various human proteins in bovine milk and the like.

Alternatively, one may wish to change the nature or characteristics of a product of a host, such as meat, vegetable oils, size, or the like. In many cases, homologous recombination will be required with both genes, since the host will be diploid. This means that one must go through an extensive number of steps in first modifying one gene, ensuring that the proper modification has occurred, then using the modified cells to repeat the process and modify the second gene. Even where the modification is a knock-out, namely introduction of an interfering sequence and/or deletion into the target locus, the process can be time-consuming and labor-intensive. There is, therefore, substantial interest in being able to develop techniques which allow for improvements in the efficiency of achieving genetic modifications at target loci.

Relevant Literature

Procedures for the modification of ES cells and detection of the modified cells may be found in Mortensen, et al., *Proc. Natl. Acad. Sci. (USA)* 88, 7036–7040 (1991). Paludan, et al., *Gene* 85, 421–426 (1989) reports enhanced resistance of cells comprising multiple neo genes. Spontaneous production of homozygous cells from heterozygous cultured cells have been reported by Nelson, et al., *Mol. Cell. Biol.* 9, 1284–1288 (1989); Potter, et al., *Proc. Natl. Acad. Sci. (USA).* 84, 1634–1637 (1987); Rajan, et al., *J. Immunol,* 145, 1598–1602 (1990) and Campbell, et al., *Mol. Cell. Biol.* 1, 336–346 (1981).

SUMMARY OF THE INVENTION

Homogenotization of gene targeting events is achieved by introducing DNA into cells, where the DNA has homology to a target locus and contains a marker gene. Cells undergoing homologous recombination are selected and subjected to elevated levels of the selection agent. Cells are then selected which have undergone gene conversion, where the mutant is now homozygous for the modification. The selective gene is normally one that imparts drug resistance and is normally incapable of amplification.

DESCRIPTION OF THE SPECIFIC EMBODIMENTS

Mutant cells which are homozygous at a targeted locus are produced by introducing DNA into the cells, where the DNA has homology to the target locus and includes a marker gene, allowing for selection of cells comprising the integrated construct. The cells are then screened for homologous recombinants. The homologous integrants are exposed to elevated levels of the marker gene, selecting for cells which have multiple copies of the selective agent by other than amplification. The cells are then analyzed for homozygosity at the target locus.

Various constructs can be prepared for homologous recombination at a target locus. Usually, the construct will include at least 50 bp of sequence homologous with the target locus and not more than 500 Kbp. The marker gene will normally be flanked on both sides by homologous sequences.

Various marker genes may be employed, which have the following characteristics. The marker gene is not amplifiable in that with increasing concentrations of the selective agent, one does not detect spontaneous events in which the gene has undergone tandem replication. The selective agent should not be extremely toxic, so that minor variations in concentration should not have significant effects on the viability of cells. Thus, one can provide for easy gradations in change of concentration of the selective agent so as to specifically select for cells having increased resistance to the selective agent. Gradations will be generally such that upon plating the heterozygous mutant at higher concentrations of the selective agent, there will colony forming efficiency of from about 1 in $10-10^5$.

The transcriptional initiation region for the marker gene may be any convenient region, either inducible or constitutive. By providing for an inducible transcription initiation region, the marker gene may be silent when the cells are introduced into a host, where the inducible agent is absent or the gene is turned on upon being introduced into a host or upon maturation and differentiation of the cells. Inducibility may be as a result of temperature, specific compounds, etc. A wide variety of promoters have been described in the literature, which are constitutive or inducible, where induction may be the result of temperature, inducing agents, any specific cell type or specific level of maturation. Also, a number of viral promoters are known, which may also find use. Promoters of interest include the β-actin promoter, SV40 early and late promoters, phosphoglycerate kinase promoter ("PGK"), immunoglobulin gene promoter, thymidine kinase promoter, human cytomegalovirus promoter and the Friend spleen focus-forming virus promoter. The promoters may or may not be associated with enhancers, where the enhancers may be naturally-associated with the particular promoter or associated with a different promoter.

A termination region will be present, where the termination region may be naturally-associated with the marker gene or may be derived from a different gene. For the most part, the termination regions are not critical and a wide variety of termination regions may be employed without adversely affecting expression or the utility of the marker gene.

DNA constructs will be prepared for integration into the target locus. The construct will comprise the marker gene, with its appropriate transcriptional and translational initiation and termination regulatory regions, flanked by regions of homology with the target locus. The integration of the subject marker gene at the target locus may interfere with functional expression in a variety of ways, preferably by insertion into the coding region or an exon of the target locus, but may also interfere by insertion into an intron where the construct has a splice-acceptor site adjacent to the marker gene, as to truncate the target locus and prevent expression of a functional protein. If one wishes, rather than providing for an independent transcriptional initiation region as part of the construct, one could provide for integration into the target locus at a site which introduces the marker gene under the transcriptional control of the transcription initiation region of the target gene, e.g. into an intron where the construct has at the 5' terminus of the marker gene a splice-acceptor site, or into an exon resulting in fusion of the reading frames of the target and marker genes. The significant factor is that integration of the marker gene at the target locus results in inactivation of the target gene.

The regions of homology with the target locus will usually be at least about 50 bp, more usually at least about 150 bp and may be as high as 500 Kbp, usually not more than about 20 Kbp, preferably not more than about 10 Kbp. Usually, there will be at least about 20, more usually at least about 50 bp of homology 5' and 3' of the marker gene. Various considerations will be involved in the extent of homology, such as the size of the target locus, availability of sequences, relative efficiency of double cross-over events at the target locus, similarity of the target sequence with other sequences, and the like.

The region(s) of homology may include mutations, where mutations may further inactivate the target gene, in providing for a frame shift, or changing a key amino acid, or the mutation may correct a dysfunctional allele, etc. Usually, the mutation will be a subtle change, not exceeding about 5% of the homologous flanking sequences, usually fewer then 50 bp. Where mutation of a gene is desired, the marker gene may be inserted into an intron, so as to be excised from the target gene upon transcription.

The construct will be prepared in accordance with known ways, where various fragments will be brought together, introduced into appropriate vectors, cloned, analyzed and then manipulated further until the desired construct has been made. Various modifications may be made to the sequence, to allow for restriction analysis, excision, identification of probes, or the like. Silent mutations may be introduced, as desired. At various stages, restriction analysis, sequencing, amplification with the polymerase chain reaction, primer repair, in vitro mutagenesis, or the like may be employed.

The construct will usually be prepared using a bacterial vector, including a procaryotic replication system, e.g. an origin recognizable by *E. coli*, where at each stage, the construct may be cloned and analyzed. A marker, the same as or different from the marker to be used for insertion, may be employed, where the procaryotic marker is usually removed prior to introduction into the target cell. Once the vector containing the construct has been completed, it may be further manipulated by deletion of the bacterial sequences, linearization, introducing a short deletion in the homologous sequence, generally not exceeding about 500 bp, generally below about 20% of the homologous sequence, usually in the range of about 50–300 bp. After final manipulation, the construct is ready to be introduced into the cell.

A wide variety of eukaryotic target host cells may be employed, normally cells from vertebrates, more particularly, mammals, desirably domestic animals or primates, particularly humans. The cells which may be subjected to transformation may be any mammalian cells of interest, which may find use in cell therapy, research, interaction with other cells in vitro or the like. Cells of particular interest include, among other lineages, stem cells, e.g. hematopoietic stem cells, embryonic stem cells, etc., the islets of Langerhans, adrenal medulla cells which may secrete dopamine, osteoblasts, osteoclasts, epithelial cells, endothelial cells, leukocytes, e.g. B- and T-lymphocytes, myelomonocytic cells, etc., neurons, glial cells, ganglion cells, retinal cells, liver cells, e.g. hepatocytes, bone marrow cells, keratinocytes, hair follicle cells, and myoblast (muscle) cells.

For embryonic stem cells, an embryonic stem cell line may be employed or embryonic stem cells may be obtained freshly from a host. The cells may be grown on an appropriate fibroblast fetal layer or grown in the presence of leukemia inhibiting factor (LIF) and then used. The embryonic stem cells may be injected into a blastocyst to provide a chimeric animal.

Upstream and/or downstream from the target gene construct may be a gene which provides for identification of whether a double cross-over has occurred. For this purpose, the herpes simplex virus thymidine kinase ("HSV-tk") gene may be employed, since the presence of the thymidine kinase gene may be detected by the use of nucleoside analogs, such as acyclovir or gancyclovir, for their cytotoxic effects on cells that contain a functional HSV-tk gene. The resistance to these nucleoside analogs indicates the absence of the thymidine kinase gene and, is therefore, indicative that a double cross-over event has occurred and -thus homologous recombination has also occurred.

Various techniques may be employed for introduction of the construct into the host cell. Techniques which may be used include calcium phosphate/DNA coprecipitates, microinjection of DNA into the cell, electroporation, lipofection, bacterial protoplast fusion with intact cells, transfection or the like. The DNA may be single- or double-stranded, linear or circular, relaxed or supercoiled DNA. For various techniques for transforming mammalian cells, see Keown, et al., *Meth. in Immun.* 185, 527–537 (1990). The cells may then be grown in appropriately-selected medium to identify cells providing the appropriate integration. Those cells which show the desired phenotype may then be further analyzed by restriction analysis, electrophoresis, Southern analysis, polymerase chain reaction, or the like. By identifying fragments which show the appropriate insertion at the target gene site, one can identify cells in which homologous recombination has occurred to inactivate or otherwise modify one of the two copies of the target gene.

The heterozygote cells containing the integrated marker gene may then be expanded in an appropriate culture medium over an extended period of time, usually at least one week and up to six weeks or more. The cells may then be plated, and individual colonies selected at varying concentrations of the drug to which the marker gene imparts resistance. For example, with neomycin resistance, depending upon the nature of the cell, the concentration of G418 may vary from about 0.5–4 mg/ml, more usually from about 0.5–2.5 mg/ml. The surviving colonies may then be screened to establish that the functional endogenous gene is absent or has been properly mutated. As described above, various techniques may be used for analyzing for the presence of homozygosity of the mutant. The resulting homozygote will have two copies of the same gene on different chromosomes, normally including the marker gene. The cell usually will otherwise be free of the construct.

The subject invention may find wide application, where one wishes to inactivate a particular gene or introduce an alteration into a gene at a target locus. Genes of interest include a variety of surface membrane protein genes. One area of interest is reduction in the expression of major histocompatibility complex antigens, Class I and/or II, or any of the individual groups, such as A, B, C, DP, DQ and DR. For knocking out Class I, one may provide for integration into the β2-microglobulin gene. For Class II antigens, it may be sufficient to knock out the DR genes. Thus, one may reduce the immunologic response associated with the presence of foreign MHC antigens, when such antigens are introduced into a host. Alternatively, one may wish to inhibit expression of the host gene when one is introducing an exogenous immunoglobulin gene, e.g. knocking out the host immunoglobulin locus, when introducing an exogenous locus. Other genes of interest include those affecting MHC expression or other components of the antigen presentation machinery of the cell which ultimately affect immunogenicity.

One may also use the subject method to study various metabolic processes, to identify the effect of the absence of a particular genetic capability, and the like. In this manner, one may be able to identify the role of particular oncogenes, the effect of regulatory proteins, the roles of enzymes, the presence of alternative pathways, and the like.

One may also use the subject methodology for introducing mutations into dysfunctional alleles, so as to cure genetic defects, particularly where subtle changes are involved such as those involving fewer than about 50 bp, frequently fewer than about 10 bp. Thus, one could modify stem cells, such as hematopoietic stem cells, to cure diseases such as sickle cell anemia, β-thalassemia, hemophelia, etc., targeting genes for gene therapy which include genes for β-globin, enzymes of erythrocyte metabolism, the complement system, coagulation factors, dystrophin, enzymes of carbohydrate, lipid, amino acid, steroid and purine and pyrimidine metabolism, transport proteins, e.g., cystic fibrosis transmembrane regulator, and the like.

The modified embryonic stem cells may be used to produce chimeric non-human mammals by injecting he homogenotized embryonic stem cells into a blastocyst and then brought to term in a female host mammal in accordance with conventional techniques. Heterozygous progeny may then be screened for the presence of the alteration at the site of the target locus, using PCR, Southern blotting or the like. After mating with a wild-type host of the same species, the resulting chimeric progeny may then be cross-mated to achieve homozygous hosts. The homozygous hosts may have a variety of alterations, where the gene at the target locus may be made non-functional, may be retained as functional, but altered, or may be retained and additional genetic capability provided, where the additional capability may be coregulated by concomitant transcription with the gene at the target locus.

The mammalian host will have target loci comprising alleles which should be at least substantially identical, in having the marker gene integrated at the same position at both alleles. In addition, any alterations as a result of the homologous recombination in the first step should also be present in both alleles. In this way a "double knockout," symmetrical integration, which may include one or more alterations at the target locus, or the like may be achieved.

The homozygotes may be subject to further genetic modification. For example, one may wish to introduce additional genetic capability into the homozygotic hosts, where the endogenous alleles have been made nonfunctional, to substitute, replace or provide different genetic capability to the host. For example, one may wish to produce human immunoglobulins in small host, such as a mouse or rabbit. By first knocking out the endogenous genes encoding for the light and heavy chains of the immunoglobulins, one can then introduce genes from the human loci, which genes encode for the human light and heavy chains and are capable of rearrangement in response to immunization of the host to produce human immunoglobulin proteins. For example, one may knockout the J regions, which prevents expression of the immunoglobulin subunits.

One may wish to remove the marker gene after homogenotization. By introducing a construct comprising substantially the same homologous DNA, possibly extended sequences, having the marker gene portion of the original construct deleted, one may be able to obtain homologous recombination with the target locus. By using a combination of marker genes for integration, one providing positive selection and the other negative selection, in the removal step, one would select against the cells retaining the marker genes. Convenient marker genes for negative selection include the herpes simplex virus thymidine kinase gene, whose presence results in sensitivity to nucleoside analogs, such as acyclovir and gancyclovir.

In bovine or ovine hosts, one may wish to replace the bovine or ovine protein with a human protein. In domestic animals, one may wish to introduce alterations which result in improved products or growth of the host. Where domestic animals are prone to diseases as a result of particular alleles, one may alter the alleles to reduce the susceptibility to the disease.

Hosts of interest include, primates other than man, ovine, bovine, equine, canine, feline, lagomorpha, murine, etc.

The following examples are offered by way of illustration and not by way of limitation.

EXPERIMENTAL

EXAMPLE I

Four separate genes, G-protein subunits $\alpha_{i2}$ and $\alpha_{i3}$, T-cell receptor (TCR)-α, β-cardiac myosin heavy chain (MYHC-B) were targeted using positive/negative selection (Mansour, et al., Nature 336, 348–352 [1988]). In each case, a targeting construct was made containing the neomycin-resistance gene (neo) driven by the promoter region of phosphoglycerate kinase (PGK) gene. The PGK-neo sequence interrupted an exon creating a detectable change in the gene's restriction enzyme digestion pattern.

In each case PGK-TK phosphoglycerate kinase promoterthymidine kinase gene) was inserted outside the regions of homology. A) The production of the $\alpha_{i2}$ target construct has been described previously in Mortensen, et al., Proc. Natl. Acad. Sci. (USA) 88, 7036–7040 (1991). B) $\alpha_{i2}$ gene clone was isolated as described for the $\alpha_{i2}$ gene. A Hind III-Sal I fragment was subcloned into Bluescript SK (+) (Stratagene). The construct contained the PGK-neo gene interrupting exon 1 at an Nco I site at the translational start ATG. C) A 5.6 Kbp fragment of the murine TCR-α gene containing all 4 constant-region exons was subcloned from genomic clone λ*1.2 into Bluescript SKII (+) (Ausubel, et al., Curr. Proto. in Mol. Biol. [John Wiley and Sons, New York, 1988]). The fragment extends from an artificial EcoRI site, 5' of the Xba I site to the XhoI site. The EcoRI site between exons 3 and 4 was deleted by digestion with EcoRI, blunting with Klenow and subsequent ligation. The first constant-region exon was interrupted at a unique EcoRV site by the insertion of PGK-neo. D) A 7.5 Kbp (SalI-EcoRV) portion of the Myhc-B gene extending from approximately exon 10 to approximately exon 24 was cloned from a Balb/c genomic library (Clontech), identity was confirmed by sequencing. A targeting construct was made by interrupting the gene at a unique Nde I site in exon 14.

ES cells (line CCE obtained from E. Robertson, Columbia University or CC1.2 obtained from A. Bradley, Baylor University) were cultured, transfected and screened for homologous recombination as previously described (Mortensen, supra [1991]). Several cell lines identified as heterozygous for homologous recombination were expanded for 14–28 days. Cell lines were then plated, cultured for 24 hours and then selected at varying concentrations of G418. DNA from the surviving clones was analyzed by Southern blot for absence of the endogenous gene.

gous recombination product, for $\alpha_{i2}$, a 13.6 Kb band, for $\alpha_{i3}$ a 6.5 band, for TCR-$\alpha$, a 2.0 band and for Myhc-B, a 7.1 band. The $\beta$-cardiac myosin probe cross-reacted with the Myhc-A ($\alpha$-cardiac myosin heavy chain), gene resulting in 2 bands being present in each lane.

To determine the frequency of homozygous mutant ES cells surviving high G418, 4 individual heterozygous subclones were isolated by plating trypsin-dispersed 17E10 cells at high dilution. Each of these subclones and the original 17E10 clones were plated $5 \times 10^5$ cells/100 mm plate, selected at high G418 levels and the surviving clones analyzed as in Table 1. Plating efficiency without G418 was 42%.

TABLE 1

Loss of heterozygosity in ES cell lines

| | | | [G418] (mg/ml) | | | |
|---|---|---|---|---|---|---|
| | | | 1.0–1.5 | | 2.0 | |
| Gene (Parent Line) | Cell Line | No. Cells Plated* | No. of Colonies | % Homozygote (No. Analyzed) | No. of Colonies | % Homozygote (No. Analyzed) |
| $\alpha_{12}$ (CCE) | 17E10 | $2 \times 10^4$ | 23 | 100% (21) | 2 | 0% (2) |
| | 18D3 | $2 \times 10^4$ | 175 | 12% (26) | 40 | ND# |
| $\alpha_{13}$ (CC1.2) | 32-32 | $1 \times 10^5$ | 100 | 53% (17) | 17 | 88% (17) |
| | 32-28 | $1 \times 10^6$ | 27 | 4% (28) | 0 | |
| TCR-$\alpha$ (CCE) | 1A4 | $5 \times 10^5$ | 37 | 43% (23) | 9 | 44% (9) |
| Myhc-b (CC1.2) | 6-6 | $5 \times 10^5$ | | | 54 | 24% (54) |
| | 6-22 | $5 \times 10^5$ | 76 | 7% (76) | 2 | 50% (2) |

*Efficiency of plating 40–80%
ND -- not determined

Southern blot analysis of DNA from the clones isolated in high concentrations of G418 was carried out. DNA was fractionated on 1% agarose gels, transferred to Genescreen and hybridized as previously described (Ausubel, supra [1988]). In each case, a band was observed for the homolo-

TABLE 2

Frequency of homozygous mutant ES cells surviving high G418

| | [G418] (mg/ml) | | | | |
|---|---|---|---|---|---|
| | 1.0 | | 2.0 | | |
| Subclone of 17E10 | No. Colonies | % Homozygote (No. Analyzed) | No. Colonies | % Homozygote (No. Analyzed) | Apparent No. of Colonies* |
| 1 | 143 | 75% (20) | 28 | 94% (18) | 114.4 |
| 2 | 152 | 92% (24) | 52 | 95% (19) | 139.3 |
| 3 | 44 | 22% (9) | 0 | | 9.8 |
| 4 | 40 | 95% (21) | 5 | 100% (4) | 38.1 |
| Average ±Std. Dev. | | | | | 75.4† ±61.4 |

*Calculated from (fraction of homozygotes at 1 mg/ml) × (total no. of colonies)
†An estimated rate of mutation per cell generation of $1.3 \times 10^{-5}$ was calculated from the number of generations since recloning (assuming a generation time of 14.2 hours$^2$ and the fraction of homozygotes [(average No. of colonies)/((No. of cells plated) × (plating efficiency))] according to the equation rate = (fraction of homozygotes)/(No. of generations since cloning). Cells were cultured for 16 days (27 generations) after plating at high dilution. Mass cultures from the original clone were selected in parallel giving 241, 261, 228, and 262 colonies per 100 mm plate containing >90% homozygotes (18 analyzed).

EXAMPLE II

Inactivation of the mouse Ig heavy chain J genes in ES cells

Construction of the inactivation vector

A 6.1-Kb EcoRI fragment, containing the mouse immunoglobulin heavy chain J region genes and flanking sequences, cloned from a Balb/c mouse embryo genomic library and inserted into pUC18 (pJH), was digested with XhoI and NaeI to delete an about 2.3 kbp fragment containing the four J genes (see Chart 2A). An about 1.1 kbp XhoI-BamHI fragment, blunted at the BamHI site, containing a neomycin resistance gene driven by the Herpes simplex virus thymidine kinase gene (HSV-tk) promoter and polyoma enhancer was isolated from pMClNeo (Thomas and Capecchi, Cell, 51, 503–512, 1987). This fragment was inserted into the XhoI-NaeI deleted pJH to form the inactivation vector (pmHδJ, see Chart 2B), in which the transcriptional orientation of the neomycin and the heavy chain genes is the same. This plasmid was linearized by NdeI digestion before transfection to ES cells. The sequences driving the homologous recombination event are about 2.8 kbp and about 1.1 kbp fragments, located 5' and 3' to the neomycin gene, respectively.

Culturing, Electroporation, and Selection of ES cells

The ES cell line E14TG2a (Koller and Smithies, 1989, *PNAS*, USA, 86, 8932–8935) was cultured on mitomycin C-treated embryonic fibroblast feeder layers as described (Koller and Smithies, 1989, *PNAS* USA, 86, 8932–8935). ES cells were trypsinized, resuspended in HBS buffer (pH 7.05; 137 mM NaCl, 5 mM KCl, 2 mM $CaCl_2$, 0.7 mM $Na_2HPO4$, 21 mM HEPES pH 7.1) at a concentration of $2\times10^7$/ml and electroporated in the presence of 50 µg/ml of the linearized inactivation vector. Electroporation was carried out with a BioRad Gene Pulser using 240 volts and 500 µF capacitance. $5\times10^6$ electroporated cells were plated onto mitomycin C-treated fibroblasts in 100 mm dishes in the presence of Dulbecco's modified Eagle's media (DMEM) supplemented with 15% fetal bovine serum and 0.1 mM 2-mercaptoethanol. The media was replaced 24 hr after electroporation with media containing 200µg/ml G418. G418-resistant ES colonies resulting 12–14 days after electroporation were picked with drawn out capillary pipettes for analysis using the polymerase chain reaction (PCR). Half of each picked colony was transferred to an individual well of a 24-well plate, already seeded with mitomycin C-treated feeder cells. The other halves, combined in pools of four, were transferred to Eppendorf tubes containing 0.3 ml of PBS and cell lysates were prepared for PCR analysis as described by Joyner et al (*Nature*, 338:153–155, 1989). The PCR reaction included 5–20 µl of the cell lysate, 1 µM of each primer, 1.5 u of Taq polymerase and 200 µM of dNTPs. The PCR amplification employed 45 cycles using a thermal cycler (Perkins-Elmer Cetus), with 1 min melt at 94° C. 2 min annealing at 55° C., and 3 min. extension at 72° C. The two priming oligonucleotides are ACGGTATCGCCGCTCCCGAT (SEQ. ID NO: 1) and AGTCACTGTAAAGACTTCGGGTA, (SEQ ID NO: 2) which correspond respectively to about 120 bases 5' of the BamHI site of the neomycin gene, and to the sequences located in the mouse heavy chain gene, about 160 bases 3' of the insertion site. Successful homologous recombination gives rise to an about 1.4 kbp fragment. 20µl of the reaction mixture is electrophoresed on 1% agarose gels, stained with ethidium bromide and transferred to nylon membranes (Gene Screen). Filters were probed with a $^{32}$P-labelled ECORI-PstI about 1.4 kbp fragment located in the mouse heavy chain, 3' of the insertion site (see Chart 2). For further analysis, genomic DNA was prepared from ES cells, digested with restriction enzymes as recommended by the manufacturers, and fragments were separated on 1% agarose gels. DNA was transferred to nylon membranes (Gene Screen) and probed with the $^{32}$P-labelled fragment as described above.

Analysis of G418-resistant ES colonies

In the first experiment, PCR analysis of the pooled colonies detected one positive PCR signal of the expected size (about 1.4 kbp) out of 34 pools representing 136 G418-resistant colonies. The four individual colonies that had contributed to this positive pool were analyzed individually by PCR, and a positive clone, ES33D5, was identified. Similar analysis of 540 G418-resistant colonies obtained in the second experiment yielded 4 additional positive clones (ES41-1), ES61-1, ES65-1, ES110-1).

In order to verify the targeting disruption of one copy of the J genes, (the gene is autosomal and thus present in two copies), the PCR positive clones were expanded and genomic DNA was prepared, digested with HindIII or with SacI and analyzed by Southern analysis as described using the EcoRI-PstI probe.

The replacement of the J genes by insertion of the neomycin gene by an homologous recombination event results in an HindIII fragment, detectable with the EcORI-PstI probe, which is about 1.9 kbp longer than the equivalent fragment in the native locus, due to the loss of two HindIII sites located in the deleted J gene region (see Chart 2C). Southern analysis of each of the 5 positive clones by HindIII digestion gave a pattern which indicated that one of the two copies of the heavy chain J genes had been disrupted. Three labeled fragments were detected: one fragment (about 760 bp), identical in size to that present in untreated cells at the same intensity, one fragment (about 2.3 kbp) identical in size to that present in untreated cells, but of decreased intensity in the PCR positive clone, and an additional fragment about 4.2 kbp, the size predicted for an homologous recombination event, present only in the PCR-positive clones. Similarly, the replacement of the J genes by the neomycin gene by an homologous recombination event results in a loss of one SacI site and the appearance of a fragment, detectable with the EcoRI-pStI probe, which is about 570 bp smaller than the equivalent fragment in the native locus (see Chart 2C). Southern analysis of the clones by SacI digestion gave the expected pattern of one native and one targeted allele: about 4.0 kbp fragment, identical in size to that detected in untreated cells, but of decreased intensity in the 5 positive clones, and an additional fragment of about 3.4 kbp, the size predicted for a targeted homologous recombination event, present only in the identified clones. Rehybridization of the Southern blots with a probe for the neomycin gene shows that only the 4.2 kbp and 3.4 kbp fragments, resulting from the HindIII and the SacI digestion, respectively, hybridized to the probe as predicted by the targeting event.

Inactivation of mouse immunoqlobulin heavy chain J genes in mice

Injection of targeted ES cells into mouse blastocysts and generation of chimeric offsprings Mice were purchased from Jackson Laboratories (Bar Harbor, Me). Three and a half day old C57BL/6 blastocysts were obtained from 4–5 week old superovulated females as described by Koller et al. 1989 supra. ES cells were trypsinized, washed once with fresh DMEM media and diluted to about 1×10⁶/ml in M2 media. About 5 µl of cells were added to a 150 µl droplet of M2 media, under paraffin oil, containing the blastocysts. Ten to fifteen cells were injected into the blastocoel of each blastocyst. Six to nine ES cell-containing blastocysts were returned to each uterine horn of C57BL/6×DBA F1 pseudopregnant females mated 2.5 days previously with vasectomized males. Pups derived from the injected blastocysts were generally born 16–18 days later. The contribution of the ES cells to the offspring was judged visually by examination of the coat color of the pups. The blastocysts were obtained from C57BL/6 mice, which are solid black in color. The ES cell line E14TG2a, the parental line from which the targeted cell lines were derived, was isolated from 129/01a mice. This mouse strain is cream in color, the combined effect of three color genes, the dominant $A^w$ allele at the agouti locus, the recessive pink-eyed-diluted allele at the p locus and the recessive $C^{ch}$ allele at the C locus. Offspring in which the ES cells participated in the formation of the animal had coats containing brown and cream hair. The ES cell line ES41-1 carrying inactivated mouse immunoglobulin heavy chain, was injected into C57BL/6 mouse blastocysts as described above. Six out of the 18 surviving pups had a high degree of coat color chimerism (70–90%). PCR analysis of DNA isolated from chimeric newborn pups from a female implanted with blastocysts injected with the inactivated ES cells, indicated that the mutated immunoglobulin heavy chain locus is present in a variety of organs such as spleen, thymus, kidney, liver, brain and skin.

Homogenotization of inactivated Ig heavy-chain J genes in ES cells

Heavy-chain J gene-targeted ES 110-1 cell line was plated on feeder cells at the density of 5×10³ cells per 100 mm plate in the presence of 1400 µg/ml of G418. Seven of the surviving colonies were expanded, genomic DNA was prepared and anlayzed by Southern analysis for the absence of endogenous Ig heavy-chain J gene. Southern analysis by Sac I digestion indicated that one of the clones, ES DK207, had lost the native Ig heavy chain locus. Hybridization of the same blot with an Xho I-Nae I probe, which spans the whole J gene region, did not detect any fragments in the ES DK207 genome, further indicating the loss of the native Ig heavy-chain allele.

Generation of chimeric mice carrying homogenotized heavy-chain targeted B cells

ES DK207 cells were injected into mouse blastocysts and chimeric mice were generated as described above. Then chimeric mice were obtained, seven of which had 40–70% coat color chimerism, indicating the ES cell contribution to these mice.

The mice were used to determine the effect of the deletion of the J genes from both heavy-chain alleles on the capability of the B cells to differentiate and express antibodies. Analysis of peripheral blood lymphocytes derived from one of these chimeras, DK334-1, indicated that about 10% of the lymphocytes are derived from the mouse strain from which the ES cells originated, namely the 129Sv\Ola strain. This was determined with Ly9a antibodies which bind to cells from strain 129, but not cells from strain C57B/6. The absence of mature B cells originating from strain 129 was established by demonstrating by means of fluorescence activated cell sorting that the lymphocytes from strain 129 lacked the surface antigens $CD45R^{bright}$ and $IgM^a$. These results support the conclusion that due to the deletion of the J region inboth alleles of the Ig heavy chain, B cell development is inhibited in lymphocytes derived from ES DK207.

It is evident from the above results, that the subject methodology provides for an effective efficient way to produce homozygosity in two or more alleles in a host, where one wishes to change the nature of one or more alleles. In this manner, one may knock out the two alleles present in a diploid host, mutate two alleles, so as to have the same sequence, while still retaining a sufficiently high frequency to allow for isolation of the desired homozygotes. The subject method can be used in a wide variety of applications, in transgenic animals, modification of the surface proteins present on a host cell, so as to reduce or enhance immunogenicity, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for making diploid mammalian cells homozygous for disrupted target loci, said method comprising:
   a. introducing into diploid mammalian cells a construct, said construct comprising a selectable marker gene flanked by regions of sequence homology to said loci, wherein said marker gene is a non-amplifiable gene which confers on said cells a preferential ability to grow in a selective medium;
   b. growing the cells obtained in step (a) in said selective medium at a first level of selective agent and analyzing viable cells to provide a population of cells which have undergone homologous recombination at one or both of the target loci;
   c. subjecting the population of cells obtained in step (b) to a level of selective agent greater that said first level, whereby cells which have undergone homologous recombination at both loci are selected; and
   d. isolating said cells obtained in step (c).

2. A method according to claim 1, wherein said marker gene is an antibiotic resistance gene.

3. A method according to claim 2, wherein said antibiotic resistance gene is a neomycin resistance gene.

4. A method according to claim 1, wherein said marker gene is flanked by at least 50 bp of sequence homologous with said target loci.

5. A method according to claim 4, wherein said homologous sequence is mutated from said target loci sequence.

6. A method according to claim 1, wherein said host cells are embryonic stem cells.

7. A method for making mammalian embryonic stem cells which are homozygous for disrupted target loci, said method comprising:
   a. introducing into mammalian embryonic stem cells a construct, said construct comprising a selectable marker gene flanked by regions of sequence homologous to said loci, wherein said marker gene is a non-amplifiable gene which confers on said cells a preferential ability to grow in a selective medium;
   b. growing the cells obtained in step (a) in said selective medium at a first level of selective agent and analyzing viable cells to provide a population of cells which have undergone homologous recombination at one or both of the target loci;
   c. subjecting the population of cells obtained in step (b) to a level of selective agent greater that said first level, whereby cells which have undergone homologous recombination at both loci are selected; and
   d. isolating said cells obtained in step (c).

8. A method according to claim 7, wherein said antibiotic resistance gene is a neomycin resistance gene.

9. A method according to claim 7, wherein said marker gene is flanked by at least 50 bp of sequence homologous with said target loci.

10. A method according to claim 9, wherein said homologous sequence is mutated from said target loci sequence.

11. A method according to claim 7, wherein said target locus is a surface membrane protein loci.

* * * * *

UNITED STATES PATENT AND TRADEMARK OFFICE
CERTIFICATE OF CORRECTION

PATENT NO. : 5,589,369
DATED : December 31, 1996
INVENTOR(S) : Seidman et al.

Page 1 of 1

It is certified that error appears in the above-identified patent and that said Letters Patent is hereby corrected as shown below:

<u>Title page,</u>
Item [75], Inventors, add -- Richard M. Mortensen, Dexter, Michigan --.

Signed and Sealed this

Sixteenth Day of May, 2006

JON W. DUDAS
*Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

ACGGTATCGC CGCTCCCGAT                     20

( 2 ) INFORMATION FOR SEQ ID NO:2:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:2:

AGTCACTGTA AAGACTTCGG GTA          23